United States Patent
Kish et al.

(10) Patent No.: US 7,229,754 B2
(45) Date of Patent: Jun. 12, 2007

(54) SENSING PHAGE-TRIGGERED ION CASCADE (SEPTIC)

(76) Inventors: Laszlo B. Kish, 1606 N. Bluebonnet Cir., College Station, TX (US) 77845; Maria Dobozi-King, 4548 Greens Prairie Tr, College Station, TX (US) 77845; Ryland Young, 916 Hawthorne St., College Station, TX (US) 77840; Mosong Cheng, 804 Royal Adelade, College Station, TX (US) 77845; James R. Biard, 207 Martha Manor, Richardson, TX (US) 75081; Sergey Bezrukov, 15779 Buena Vista Dr., Derwood, MD (US) 20855

( * ) Notice: Subject to any disclaimer, the term of this patent is extended or adjusted under 35 U.S.C. 154(b) by 0 days.

(21) Appl. No.: 11/286,621

(22) Filed: Nov. 23, 2005

(65) Prior Publication Data

US 2007/0111220 A1    May 17, 2007

Related U.S. Application Data

(60) Provisional application No. 60/630,975, filed on Nov. 24, 2004.

(51) Int. Cl.
   *C12Q 1/70* (2006.01)
(52) U.S. Cl. ........................ 435/5; 435/287.1
(58) Field of Classification Search ............... None
   See application file for complete search history.

(56) References Cited

U.S. PATENT DOCUMENTS 6,210,910 B1   4/2001   Walt et al.

OTHER PUBLICATIONS

Daugelavičius et al. Changes in host cell energetics in response to bacteriophage PRD1 DNA entry J. Bacteriol., vol. 179, No. 16 (Aug. 1997), pp. 5203-5210.*
Grahn et al. "The Small Viral Membrane-Associated Protein P32 Is Involved in Bacteriophage PRD1 DNA Entry" Journal of Virology, vol. 76, No. 10 (May 2002), p. 4866-4872.*
Labedan et al. "Membrane potential changes during the first steps of coliphage infection" Proc. Nat. Acad. Sci. USA, vol. 78, No. 1 (Jan. 1981), pp. 215-219.*
Cheng, L.-T., S. Hupfer, S. Ross, and J. Patterson, Jazzing up Eclipse with collaborative tools, *Proc. of the 18th Annual ACM SIGPLAN Conf. on Object-Orientd Programming, Sys., Languages, and Applications / Eclipse Technology Exchange Workshop*, Anaheim, CA, Oct. 27, 2003, pp. 45-49.
Dwyer, T., Collaboration and modeling solutions integrate with new tools to bolster developer productivity, *Yankee Group*, Sep. 2005, available at http://developers.sun.com/prodtech/javatools/jsenterprise/reference/whitepapers/YankeeGroup.pdf.
Srivastava, A., J. Thiagarajan, C. Schertz, Efficient integration testing using dependency analysis, MSR-TR-2005-94, Jul. 2005.
Venolia, G., Bridges between silos: A Microsoft research project, Microsoft Research Software Improvement Group, Jan. 2005.
PCT International Search Report for PCT/US05/42832 dated Jun. 27, 2006.

* cited by examiner

*Primary Examiner*—Bruce R. Campell
*Assistant Examiner*—Stuart W. Snyder
(74) *Attorney, Agent, or Firm*—Edwin S. Flores; Chalker Flores, LLP

(57) ABSTRACT

The present invention provides a method for detecting bacteria and a nano-well device having one or more input/output connections about a gap and one or more bacteriophages at or about the gap that trigger a detectable electrical field fluctuation when the one or more bacteriophages contact a cognate target within a liquid sample.

23 Claims, 7 Drawing Sheets

SENSING PHAGE-TRIGGERED ION CASCADE (SEPTIC)

TECHNICAL FIELD OF THE INVENTION

The present invention relates in general to the field of ionic sensing, and more particularly, to an apparatus, method and system for the detection and identification of bacteria using phage induced ion channels.

BACKGROUND OF THE INVENTION

This application claims priority to U.S. Provisional Patent No. 60/630,975, filed Nov. 24, 2004, incorporated herein by reference in its entirety. This invention was made with U.S. Government support under U.S. Army Medical Command, as part of the project "Detection and Remediation of Chemical Threat Agents" (TEES 32536/5975Q). The government has certain rights in this invention. Without limiting the scope of the invention, its background is described in connection with bacterial detection.

Bacteriophages are viruses that kill bacteria. Most bacteriophages have defined host-specificity, a characteristic that has led to the widespread use of bacteriophages for typing of pathogenic bacteria ("phage typing"; see, 1–3, 6, 8, 11, 12). Double-stranded DNA phages can be grouped into three main morphotypes: myophages, which have contractile tails; siphophages; which have flexible, non-contractile tails, and podophages, which have short, "stumpy" tails.

Bacteriophages are the most numerous biological entities, estimated at $10^{31}$ in the biosphere, and are unimaginably diverse. Phages exist with a wide range of host specificities, from narrow host range phages like λ, which infects only some strains of *E. coli*, to generalists like P1, which can inject its DNA into all enterobacteria and even myxobacteria. Consequently, phages have long been used as a "low-tech" method to type bacteria in clinical microbiology environments. Attempts to exploit the specificity of phages in detection and identification of pathogenic bacteria have been burdened by the requirement of culturing the target bacteria, growing the infected culture, and assaying the production of progeny virions, processes which at minimum require hours and also knowledge of the culture conditions is required.

The committed step in bacteriophage infection is irreversible adsorption. For double-stranded DNA (dsDNA) phages, the results from interactions between the specific adsorption apparatus, usually tail fibers, with specific receptors on the surface of the host cell. For two of the three main morphotypes of dsDNA phages, the myophages with contractile tails and the siphophages with flexible tails, the injection of DNA into the host cell follows rapidly and involves the transitory formation of a channel through which the phage DNA passes into the target cytoplasm. Concomitant with injection is a short-lived membrane depolarization and an efflux of $K^+$ ions from the cytoplasm, at a rate of $\sim 10^6$/sec per infected cell, before a poorly-understood re-sealing process occurs, allowing re-energization of the membrane and the commencement of the infection program.

SUMMARY OF THE INVENTION

The present invention is an apparatus, system and method (e.g., a biochip) for the detection and identification of bacteria. One advantage of the present invention is that the detection of the bacteria requires only irreversible attachment of the phage virions to the bacterial targets. As soon as the adsorption occurs, the injection events cause a transitory leakage of ions that constitute the local perturbations in the electric field. Thus, these designs do not require growth of the bacteria or the ability of the phage to propagate.

In many cases, bacteria have "restriction systems" that allow phages to adsorb and inject DNA, but which then destroy the injected DNA and prevent phage growth. All systems using the growth of phages to detect bacteria are subject to this limitation, but the current design is not. This event happens without regard to whether the bacteria are growing. Other advantages that will accrue for the fully developed system: portability, speed, reliability/accuracy, and low-cost. The present system requires specific bacteriophages for each bacterial strain to be detected, however, the present invention allows for the isolation and characterization of new bacteriophages.

In one embodiment, the present invention includes an apparatus and method for the detection of bacteria and/or viruses (e.g., bacteriophages) that includes a nano-well device comprising input/output connections about a gap; and a bacteriophage or bacteria or both at or about the gap, wherein electrical field fluctuations in a fluid at the gap demonstrate the present of absence of a bacteria exposed to the bacteriophage.

The present invention includes a nano-well device and method for detecting bacteria. The present invention includes an apparatus including a nano-well device having one or more input/output connections about a gap and one or more bacteriophages at or about the gap that trigger a detectable electrical field fluctuation when the one or more bacteriophages contact a cognate target within a liquid sample.

The present invention also provides a method for detecting bacteria. The method includes contacting a nano-well device having one or more input/output connections about a gap with one or more bacteriophages at or about the gap with a liquid sample and detecting one or more electrical field fluctuations produced when one or more bacteriophages contact a cognate target within the sample, whereby the one or more electrical field fluctuations in the sample at the gap demonstrate the present of absence of the cognate target within the sample.

The present invention includes a nano-well sensor having a substrate and a nanowell device disposed on the substrate. The nanowell device includes one or more input/output connections about a gap and one or more bacteriophages at or about the gap that trigger a detectable electrical field fluctuation when the one or more bacteriophages contact a cognate target within a liquid sample.

A method for making a nano-well sensor is also included. The nano-well sensor is made by forming on a substrate one or more input/output connections about a gap. One or more bacteriophages are provided at or about the gap that trigger a detectable electrical field fluctuation when the one or more bacteriophages contact a cognate target within a liquid sample.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "depositing" refers to the placing or setting down of a layer or the laying down or leaving behind by a process. A variety of mechanisms may be used to deposit one or more layers including one or more layers comprising electroplating, vapor deposition, spin coating, coating, sputtering, in-situ polymerization or combinations thereof. The layer may be homogeneous or heterogeneous in nature. Additionally, the layer that is deposited may include a metal, a nonmetal, a polymer, a composite, a resist, a resin, a carbon nano-tube, a plastic or combinations thereof.

As used herein, the term "metal" or "metal containing" refers to gold, silver, platinum, copper, aluminum, tungsten, titanium, tantalum, molybdenum, chromium, ruthenium, rhodium, palladium, iridium, nickel or the like, alloy thereof or combinations thereof. The metal compound may be titanium nitride, titanium tungsten, tantalum nitride, tungsten nitride, molybdenum nitride or the like. As used herein, the term "etching" refers to the cut into or removing entirely or partially from a surface, e.g., reactive ion etching.

As used herein, the term "exposing" or "expose" is defined as the removal of a portion of one or more areas. The area may be on a side portion of the one or more pins, on the tip of the pin or combination thereof. The removal may occur through chemical and/or mechanical planarization, laser ablation or chemical removal.

As used herein, the term "substrate," is defined as an underlying layer and the surface on which a material is deposited. The substrate may be partially transparent substance including glass, plastic, polymer, quartz or combinations thereof. The substrate may include one or more bioactive agents, biodegradable, electrically conductive, thermally conductive, porous, stimulatable, or combinations thereof.

The pads of the present invention may be attached using any of a number of known bonding techniques, such as, but not limited to, wire bonding, flip-chip bonding and tape-automated bonding. When used as part of a "probe", these contact pads will generally have a high surface area to maximize a signal that is being detected at the probe surface. In one example, a ball or solder bond made of aluminum, gold, copper, solder, or like materials is bonded to the contact pad. When wire bonding the site of contact may be referred to as a chisel bond. The contact pad(s) are exposed and uncovered. The contact pad and/or the layer it is formed from may be made from a conductive material such as a semiconductor and/or a conductive metal, e.g., aluminum and/or copper. It is common to place a reinforcement layer under the contact pad layer. Examples of reinforcement layers are those that are made from a strong, "refractory" metal, such as titanium, titanium nitride, tungsten, tungsten nitride, nickel, nickel nitride, tantalum, tantalum nitride, tantalum silicon nitride, and combinations/alloys thereof.

Examples of phage that may be used in conjunction with the present invention includes all those that are or may become available with a known bacterial target as will be known to those of skill in the art. For example, a list of phage types available from the American Type Culture Collection (ATCC) as published in the Catalog of Bacteria & Bacteriophages. Other such depositories also publish equivalent data in their catalogues and this may be used to identify possible phage for use with the present method. Phages may be used, inter alia, in aqueous or other suspension and may even provided in freeze-dried form, spray-dried, vacuum dried and other forms are part of, e.g., microtiter plates that include within the wells the input/output pads of the present invention. Generally, the phage are lytic and may lead to lysis of the target organism, however, for certain applications the phage may be defective and only provide the required ionic signal produced upon contact and injection into the cytoplasm of their target.

The present invention includes a nano-well device and method for detecting bacteria. The present invention includes an apparatus including a nano-well device wherein one or more bacteriophages trigger a detectable electrical field fluctuation when the one or more bacteriophages contact a cognate target within a liquid sample.

The present invention provides a bacterium detection and identification method "SEnsing of Phage-Triggered Ion Cascade (SEPTIC)" which is able to identify living bacteria within a few minutes time with specificity. The method utilizes the fact that, after bacteriophage infection, the bacteria emit about $10^8$ ions into the ambient fluid and the voltage fluctuations induced by this ion emission can be detected with two thin metal film electrodes of a size of a few microns.

For example, the present invention provides an apparatus including a nano-well device having one or more input/output connections about a gap and one or more bacteriophages at or about the gap that trigger a detectable electrical field fluctuation when the one or more bacteriophages contact a cognate target within a liquid sample. The gap is between about 50 to about 500 nanometers and the one or more input/output connections include a FET, a JFET, a MOSFET, an OSFET or an SPR sensor connected using ball bonds, wire bonds, tape bonds, chisel bonds and combinations thereof. In addition, the one or more input/output connections are in electrical communication with an amplifier, a preamplifier, a contact, a switch, a transistor and combinations thereof.

The contact between the one or more bacteriophages and the cognate target causes stochastic waves with various time and amplitude scales. The detectable electrical field fluctuation that are produced include a power density spectra of about $1/f$, $1/f^2$ shape and combinations thereof. The contact between the one or more bacteriophages and the cognate target causes one or more stochastic fluctuations have a power spectra with approximately an $1/f^2$ shape in the frequency range of about 1 Hz and about 10 Hz.

The cognate target for the phage include *Escherichia, Enterobacter, Salmonella, Staphylococcus, Shigella, Listeria, Aerobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia* phage, *Chromobacterium, Brucella, Yersinia, Haemophilus, Bordetella* and combinations thereof and the one or more bacteriophages include *S. mutans* phages, *Bacillus* phage Φ29, *Actinomyces* phages, bacteriophage M102, bacteriophage e10, bacteriophage f1, bacteriophage λ, bacteriophage PI, spherical phage PhiXI74, spherical phage G4, spherical phage S13, bacteriophage T1, bacteriophage T2, bacteriophage T3, bacteriophage T4, bacteriophage T5, bacteriophage T6, bacteriophage T7, ssRNA bacteriophages MS2, ssRNA bacteriophages R17, ssRNA bacteriophages f2, ssRNA bacteriophages Q beta and combinations thereof.

The present invention also provides a method for detecting bacteria by contacting a nano-well device having one or more input/output connections about a gap with one or more bacteriophages at or about the gap with a liquid sample and detecting one or more electrical field fluctuations produced when one or more bacteriophages contact a cognate target within the sample, whereby the one or more electrical field fluctuations in the sample at the gap demonstrate the present of absence of the cognate target within the sample.

The contact between the one or more bacteriophages and the cognate target causes one or more stochastic fluctuations comprising a power spectra with approximately an $1/f^2$ shape in the frequency range of about 1 Hz and about 10 Hz. The cognate target includes one or more bacteria selected from *Escherichia, Enterobacter, Salmonella, Staphylococcus, Shigella, Listeria, Aerobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia* phage, *Chromobacterium, Brucella, Yersinia, Haemophilus, Bordetella* and combinations thereof and the bacteriophages include *S. mutans* phages, *Bacillus* phage Φ29, *Actinomyces* phages, bacteriophage M102, bacteriophage e10, bacteriophage f1, bacteriophage λ, bacteriophage PI, spherical phage PhiX174, spherical phage G4, spherical phage S13, bacteriophage T1, bacteriophage T2, bacteriophage T3, bacteriophage T4, bacteriophage T5, bacteriophage T6, bacteriophage T7, ssRNA bacteriophages MS2, ssRNA bacteriophages R17, ssRNA bacteriophages f2, ssRNA bacteriophages Q beta and combinations thereof.

The present invention includes a nano-well sensor having a substrate and a nanowell device disposed on the substrate. The nanowell device includes one or more input/output connections about a gap and one or more bacteriophages at or about the gap that trigger a detectable electrical field fluctuation when the one or more bacteriophages contact a cognate target within a liquid sample.

The present invention provides a method for making a nano-well sensor by forming on a substrate one or more input/output connections about a gap and providing one or more bacteriophages at or about the gap that trigger a detectable electrical field fluctuation when the one or more bacteriophages contact a cognate target within a liquid sample.

The substrate includes glass, plastic, polymer, quartz, silicon, sapphire, quartz, silica, silicon carbide, zinc oxide, magnesium oxide, manganese oxide, germanium, gallium nitride, gallium arsenide, gallium phosphide or a metal or combinations thereof and the one or more input/output connections may be formed by electroplating, vapor deposition, spin coating, coating, sputtering, in-situ polymerization or combinations thereof. The one or more input/output connections comprise a metal, a nonmetal, a polymer, a composite, a resist, a resin, a carbon nano-tube, a plastic or combinations thereof. In addition, an insulating layer deposited on at least a portion of the one or more input/output connections with a gap positioned for exposure to the liquid sample.

The cognate target for the phage includes one or more bacteria selected from *Escherichia, Enterobacter, Salmonella, Staphylococcus, Shigella, Listeria, Aerobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia* phage, *Chromobacterium, Brucella, Yersinia, Haemophilus, Bordetella* and combinations thereof and the one or more bacteriophages include *S. mutans* phages, *Bacillus* phage Φ29, *Actinomyces* phages, bacteriophage M102, bacteriophage e10, bacteriophage f1, bacteriophage λ, bacteriophage PI, spherical phage PhiXI74, spherical phage G4, spherical phage S13, bacteriophage T1, bacteriophage T2, bacteriophage T3, bacteriophage T4, bacteriophage T5, bacteriophage T6, bacteriophage T7, ssRNA bacteriophages MS2, ssRNA bacteriophages R17, ssRNA bacteriophages f2, ssRNA bacteriophages Q beta and combinations thereof.

Figure 1A:
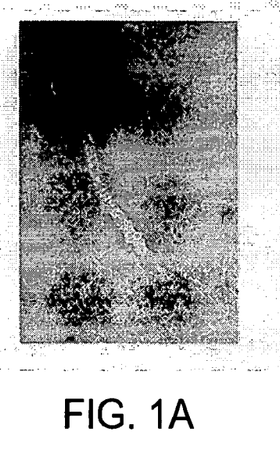
FIG. 1 shows three different phage morphologies.
Figure 1B:
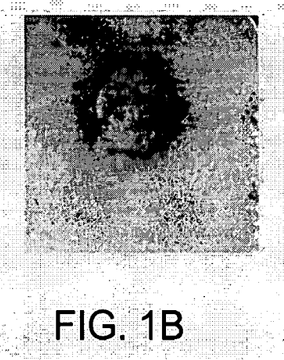
Figure 1C:
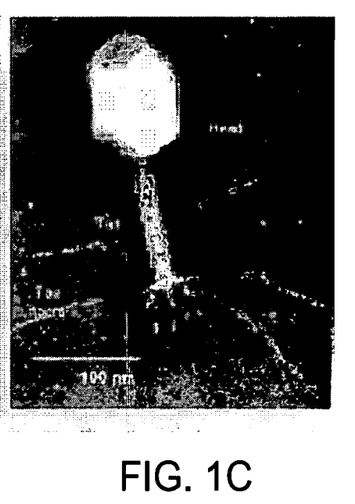

FIGS. 1A, 1B and 1C are an electron microscope images showing three different bacteriophage morphologies. FIG. 1A is a bacteriophage λ "siphophage" that has a 50 nm icosahedral head with about 48.5 kb DNA and a 150 nm flexible tail. The bacteriophage λ also has four side tail fibers. FIG. 1B is a bacteriophage T7 "podophage" that has a 60 nm icosahedral head with about 40 kb DNA and a 20 nm stubby tail. The bacteriophage T7 has a tail spike and six tail fibers. FIG. 1C is a bacteriophage T4 "myophage" that has an 80 nm×110 nm elongated icosahedral head with about 170 kb DNA and an 115 nm contractile tail. The bacteriophage T4 has six tail short fibers and six long tail fibers. In addition to bacteriophage λ, bacteriophage T7 and bacteriophage T4, other bacteriophages may be used in the present invention, e.g., *S. mutans* bacteriophages, *Actinomyces* bacteriophages, *Bacillus* bacteriophage Φ29, bacteriophage M102, bacteriophage e10, bacteriophage f1, bacteriophage PI and combinations thereof. In addition, the skilled artisan will recognize the numerous other bacteriophages that may be used in the present invention to attract the desired cell/strains.

For all of these phage types, the adsorption to the bacterial cell surface is defined by simple two-body collision kinetics, with rate constants ranging from about $10^{-10}$ to about $10^{-12}$ ml cell$^{-1}$ sec$^{-1}$. Hence, at about $10^9$ phage particle/ml, an easily achievable concentration, >about 90% of the target bacteria can be infected within seconds to a few minutes, irrespective of the bacterial cell concentration and with complete specificity (i.e., non-target bacteria have no effect on the adsorption rate or specificity). For the myophages and siphophages, the process by which phage DNA is transported through the bacterial cell envelope is rapid and highly efficient (7).

For these types of phages (but not podophages), multiple lines of evidence, including transmission electron microscopy and electrophysiology, indicate that there is a transitory channel formed in the cytoplasmic membrane through which the DNA passes. This channel causes a transitory depolarization of the host cytoplasmic membrane, which normally is maintained at about −180 mV (positive outside) (5, 9). After the DNA reaches the cytoplasm, the phage particle causes the channel to be sealed, allowing the host membrane to return to its normal state of energization, and the infection cycle proceeds. During the period while the channel is open, a substantial flow of ions occurs across the membrane and into the ambient fluid, presumably through the channel (4).

The emitted ions will undergo rapid Brownian motion around the bacterium and many will be able to escape from the vicinity of the bacterium. This fact and the charge-imbalance of the emission of the different ion ensembles will cause temporary charging and temporal charging fluctuations of the bacterium. This temporarily non-neutralized charging and the randomness of the timing and the spatial orientation of the ion emission, and that of the Brownian motion of emitted ions, will yield stochastic spatiotemporal electrical field fluctuations at the micron or submicron scale. Based on decades of study of bacteriophage infection, indicates that these electrical field fluctuations can be detected by nanoscale detector structures.

To reproduce and establish the generality of the infection-associated ion efflux, initial studies were performed with bacteriophages λ (λ Δstf tfa::cat cI857 S105, lacking tail fibers), and Ur-λ (λ wt, possessing tail fibers), using low motility *Escherichia coli* W3110 (ΔfhuA) strain ($\lambda^s$) as host. As resistant strain, isogenic host mutant strain $\lambda^R$ (*E. coli* W3110 ΔfhuA ΔlamB), was used, where the appropriate phage receptors were missing. The deletion of the lamB gene confers absolute resistance to the phage, therefore no injection leakage of ions was anticipated. In one example, the bacteriophage T5, the wild type *E. coli* strain W3110 was used as the sensitive host ($T5^s$) and the isogenic host mutant strain *Escherichia coli* W3110 (ΔfhuA) as resistant strain ($T5^R$). Protocols based on the classic work of Boulanger and Letellier (1988) were followed. The basic protocol included mixing the purified phage stock (e.g., about $2\times10^{10}$ pfu/ml) with the host cells (e.g., mid-log phase cells, washed and resuspended in 5 mM $MgSO_4$) in equal ratio, at time zero, incubate at about 37° C. for various times, apply aliquots (e.g., 5 μl) on the chip and measure the fluctuations due to ion release, over a period of time (e.g., two minutes).

The present invention includes a specially designed nano-well device and includes a lateral, micron-size capacitor of titanium electrodes with gap size of about 100 nm to measure the electrical field fluctuations in the fluid in the vicinity of bacterial cells of the well-studied laboratory bacteria, *Escherichia coli*. Before the infection of the bacteria, the electrical field fluctuations were small and their power density spectra had approximately 1/f shape. After the phage invasion, large and slow stochastic waves with various time and amplitude scales are observed. These fluctuations had power spectra with approximately $1/f^2$ shape in the frequency range of about 1 to about 10 Hz. Important control studies with bacteria that are resistant to the test phages (i.e., bacteria which do not have the specific phage receptor on their surface) did not show either the increase of fluctuations or the slow wave fluctuation dynamics.

Electrical field fluctuations were detected by a special purpose nano-well device. The patterning of nano-well sensor device includes two processes: first, Electron Beam Lithography (EBL) is used to write the nano-well (150 nm*60 μm); then contact photolithography is used to pattern two large contact pads (5 mm*5 mm) and a bridge (100 μm*4 μm) that connects the two pads. The pads are used for electrical connections with external circuitry, while the bridge connects the pads with the nano-well.

Figure 2A:
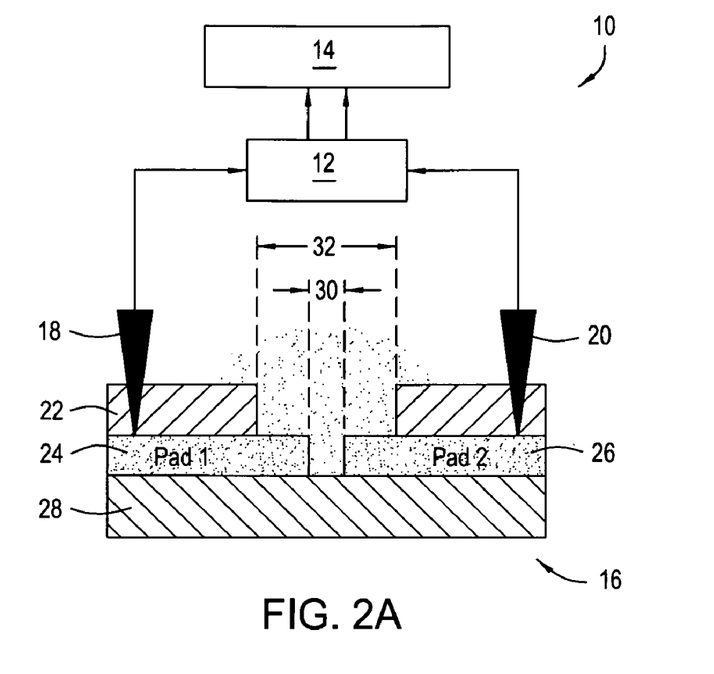
FIG. 2A is a side view and FIG. 2B is a top-view of the chip with a nano-well, contact pads, and bridges that connect the pads with the nano-well.
Figure 2B:
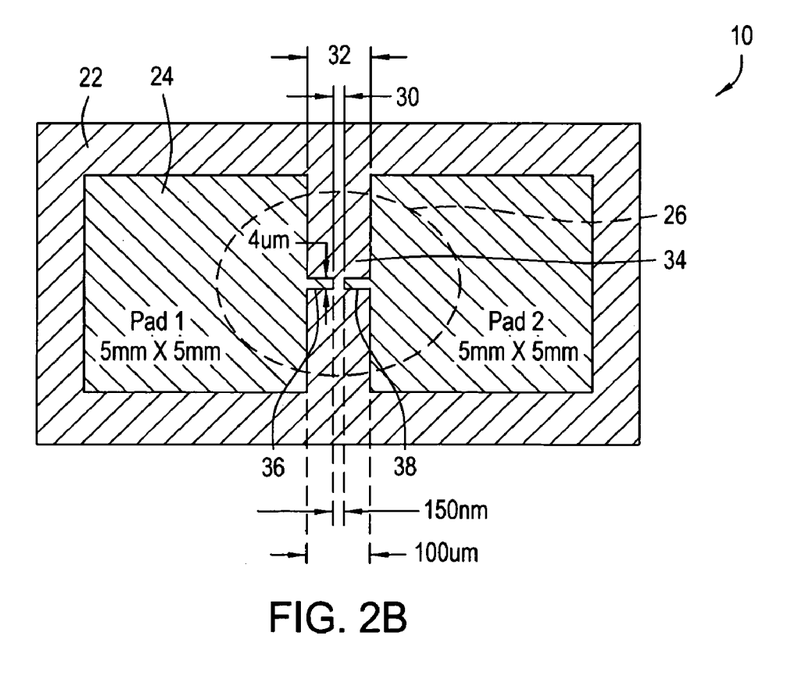

The profile and top-down view of the chip are illustrated in FIGS. 2A and 2B. FIG. 2A is a side view of one embodiment of the nanoscale detector. The nanoscale detector 10 includes a preamplifier module 12, a signal acquisition module 14 and a nano-well sensor device 16. The signal acquisition module 14 is in communication with the preamplifier module 12. The communication may be directly wired, connected through a network (e.g., wireless or wired) or stored on electronic media to be later communicated. The preamplifier module 12 is connected to at least a first probe 18 and a second probe 20 which are in communication with the nano-well sensor device 16. The preamplifier module 12 may be connected to numerous probes, e.g., 1, 2, 3, 4, 5, 6, 7, 8, 9, 10, 11 or more probes. The first probe 18 at least partially penetrates a photoresist coating 22 to contact a first contact pad 24. The second probe 20 at least partially penetrates a photoresist coating 22 to contact a second contact pad 26. The first contact pad 24 and the second contact pad 26 are on a substrate layer 28. The first contact pad 24 and second contact pad 26 are positioned on the substrate layer 28 to form an electrode gap 30. The photoresist coating 22 has a photoresist gap 32 that separates the first probe 18 and the second probe 20. In one example, the signal acquisition module 14 is a ML750 Powerlab/4sp and the preamplifier module 12 is a SR560; however, the skilled artisan will recognize that other preamplifier and signal acquisition modules may be used.

The photoresist gap 32 in one example is 8 μm; however, the photoresist gap 32 may be between 2 μm and 16 μm. The electrode gap 30 is 150 nm but may be between about 100 nm and about 200 nm depending on the particular application. The photoresist gap 32 and the electrode gap 30 are positioned to contact a liquid sample.

FIG. 2B illustrates a circuit using the present nanoscale detector. FIG. 2B is a top view of the nano-well sensor device 16 of the present invention. A photoresist coating 22 at least partially covers a first contact pad 24 and a second contact pad 26. The first contact pad 24 and the second contact pad 26 are on a substrate layer (not shown). The first contact pad 24 and second contact pad 26 are positioned on the substrate layer (not shown) to form an electrode gap 30. The photoresist coating 22 has a photoresist gap 32 that separates the first contact pad tip 36 and the second contact pad tip 38, which in turn separate the first probe (not shown) and the second probe (not shown). The first probe (not shown) and the second probe (not shown) are connected to an electrical circuit in the form of a preamplifier module (not shown) or other circuit (not shown). The nano-well is actually a 150 nm wide and 4 μm long gap in the middle of the bridge, as indicated by FIG. 2B. The photoresist gap 32 and the electrode gap 30 are positioned to contact a liquid sample.

The photoresist gap 32 in one example is 8 μm; however, the photoresist gap 32 may be between 2 μm and 16 μm. The electrode gap 30 is 150 nm but may be between about 100 nm and about 200 nm depending on the particular application. An analyte window 34 is positioned in the photoresist coating 22 above a first contact pad tip 36 that is a part of the first contact pad 24 and a second contact pad tip 38 that is a part of the second contact pad 26. At least a portion of the first contact pad tip 36 and second contact pad tip 38 extends into the analyte window 34. The first contact pad tip 36 and second contact pad tip 38 may be of any dimensions needed, e.g., a width of about 4 µm and a length of about 8 µm. Generally the analyte window 34 is 8 µm×6 µm; however the skilled artisan will recognize the window may be smaller or larger.

The voltage fluctuations induced on the nano-well device 16 by the electrical field were amplified by a low-noise preamplifier 12 SR560 with high input impedance (about 100 MOhm) and fed into signal acquisition unit 14 ML750 PowerLab/4SP as illustrated in FIG. 2. The power density spectrum of the fluctuations was determined by a Dynamic Signal Analyzer SR785 (not shown). In one embodiment the nano-well device 16 was placed in a double screening box (Amuneal Manufacturing Corp.) (not shown). The double screening box (not shown) and the preamplifier 14 were placed on an anti-vibration platform 100BM-2 (Nano-K) (not shown) to avoid potential artifacts caused by vibrations. The time window of the determination of the power density spectrum Su(f) was about two minutes.

Figure 3A:
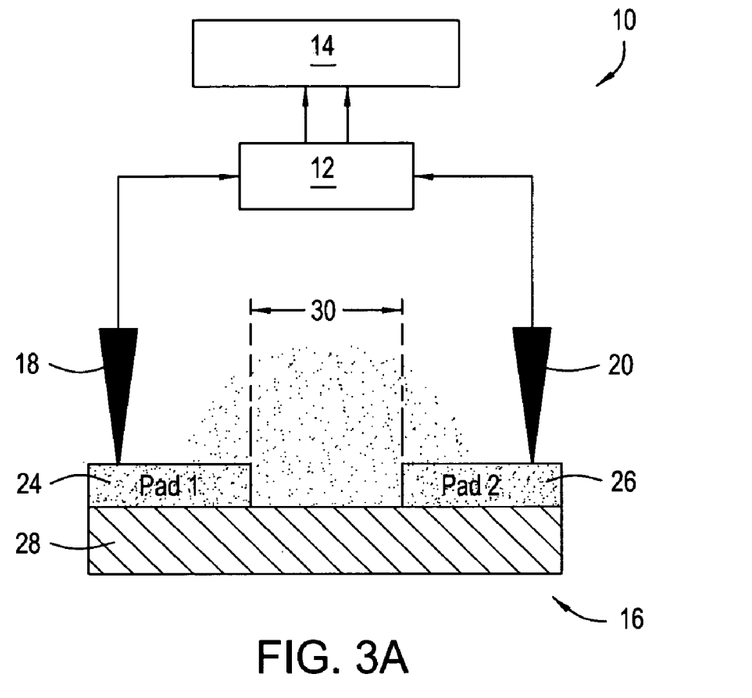
FIG. 3A is a side view and FIG. 3B is a top-view of the chip with a micro-well which has a 100 μm gap and contact pads without the bridge structures.
Figure 3B:
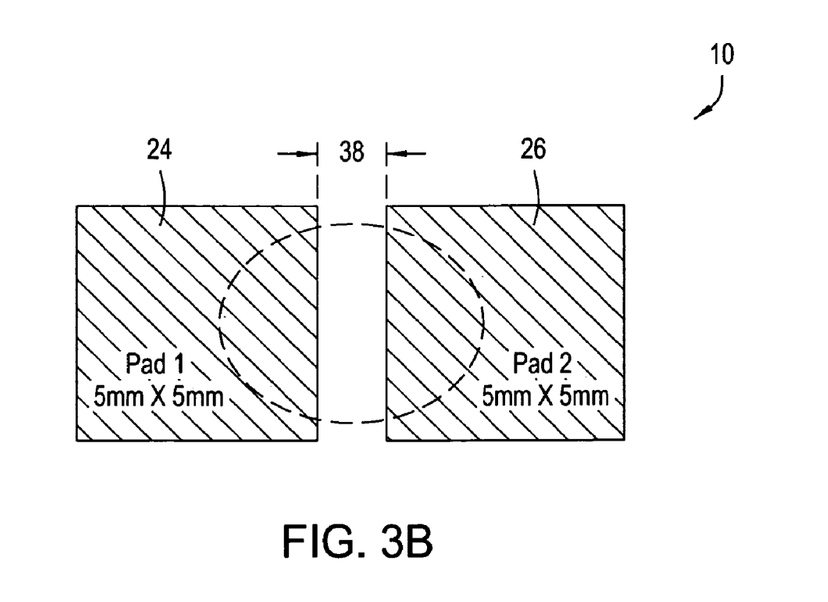

The profile and top-down view of the chip are illustrated in FIGS. 3A and 3B. FIG. 3A is a side view of another embodiment of the nanoscale detector. The nanoscale detector 10 includes a preamplifier module 12, a signal acquisition module 14 and a nano-well sensor device 16. The signal acquisition module 14 is in communication with the preamplifier module 12. The communication may be directly wired, connected through a network (e.g., wireless or wired) or stored on electronic media to be later communicated. The preamplifier module 12 is connected to at least a first probe 18 and a second probe 20 which are in communication with the nano-well sensor device 16. The preamplifier module 12 may be connected to numerous probes, e.g., 1, 2, 3, 4, 5, 6, 7, 8, 9, 10, 11 or more probes. The first probe 18 at least partially contacts a first contact pad 24. The second probe 20 at least partially contacts a second contact pad 26. The first contact pad 24 and the second contact pad 26 are on a substrate layer 28. The first contact pad 24 and second contact pad 26 are positioned on the substrate layer 28 to form an electrode gap 30. In one example, the signal acquisition module 14 is a ML750 Powerlab/4sp and the preamplifier module 12 is a SR560; however, the skilled artisan will recognize that other preamplifier and signal acquisition modules may be used. The electrode gap 30 is positioned to contact a liquid sample.

FIG. 3B is a top view of the nano-well sensor device 16 of the present invention. The first contact pad 24 and the second contact pad 26 are on a substrate layer (not shown). The first contact pad 24 and second contact pad 26 are positioned on the substrate layer (not shown) to form an electrode gap 30. The electrode gap 30 is positioned to contact a liquid sample.

The electrode gap 30 is 100 µm but may be between about 60 nm and about 200 nm depending on the particular application. The first contact pad 24 and the second contact pad 26 provide a gap electrode 30. At least a portion of the first contact pad 24 and the second contact pad 26 contact an analyte or liquid sample (not shown).

In one example, the substrate layer 28 is a silicone substrate; however, the substrate layer 28 may also be glass, plastic, polymer, quartz, silicon, sapphire, quartz, silica, silicon carbide, zinc oxide, magnesium oxide, manganese oxide, germanium, gallium nitride, gallium arsenide, gallium phosphide or a metal or combinations thereof. In addition, the substrate may include one or more agents that are bioactive, electrically conductive, thermally conductive, porous, or combinations thereof.

The first contact pad 24 and/or the second contact pad 26 are titanium; however, the contact pads may individually be a metal, a nonmetal, a polymer, a composite, a resist, a resin, a carbon nano-tube, a plastic or combinations thereof. Additionally, the one or more layers may be bioactive, biodegradable, electrically conductive, thermally conductive, porous, stimulatable, or combinations thereof. In addition, more than one layer may be deposited. For example, a second layer of material may be deposited onto the contact layer and the materials may be of dissimilar materials. Alternatively, the contact layer may be of dissimilar materials to produce a first contact pad and a second contact pad of different material. The contact layer may be deposited through a variety of methods including, e.g., electroplating, vapor deposition, spin coating, coating, sputtering, in-situ polymerization or combinations thereof.

In one embodiment of the present invention titanium may be used as a material for the contact layer and in turn the first contact pad and the second contact pad; however, other metals, alloys, doped materials, conductive polymers or metal containing compounds may be used, e.g., gold, silver, platinum, copper, aluminum, tungsten, tantalum, molybdenum, chromium, nickel or the like, alloy thereof or combinations thereof. The metal compound may be titanium nitride, titanium tungsten, tantalum nitride, tungsten nitride, molybdenum nitride or the like.

In addition, the present invention includes the photoresist coating 22 which in one example is AZ5214 under the brand name of Hekisuto K.K.; however, the skilled artisan will recognize that the photoresist coating may be photoimagable polyimides, photoimagable benzocyclobutenes, photoimagable epoxies, novolac based positive photoresists, cardo type photopolymers, A4110, AZ1370 and the like.

In certain steps etching is preformed and may be accomplished through any compatible technique known to the skilled artisan, e.g., reactive ion etching, $Cf_4/O_2$ plasma. For example, a Plasma-Therm 790 System may be used at etching conditions of about 150 mbar, 16 standard cubic centimeters per minute (sccm) of $CF_4$ and 0.12 watts per centimeter squared for a total of about five to ten minutes although other suitable parameters may also be used.

In addition to the nanometer scale design of the present invention (e.g., nano-well design) the present invention also includes a much larger detector, e.g., a micro-well. The micro-well is similar to the nano-well, except for the contact area with galvanic coupling between the fluid and the preamplifier is 500,000 larger. FIG. 3 depicts the profile and top-down view of the micro-well chip. With the nano-well, in the presence of non-adsorbing phages and bacteria, the electrical field fluctuations were small, displaying power density spectra of approximately 1/f shape (FIG. 4).

Figure 4:
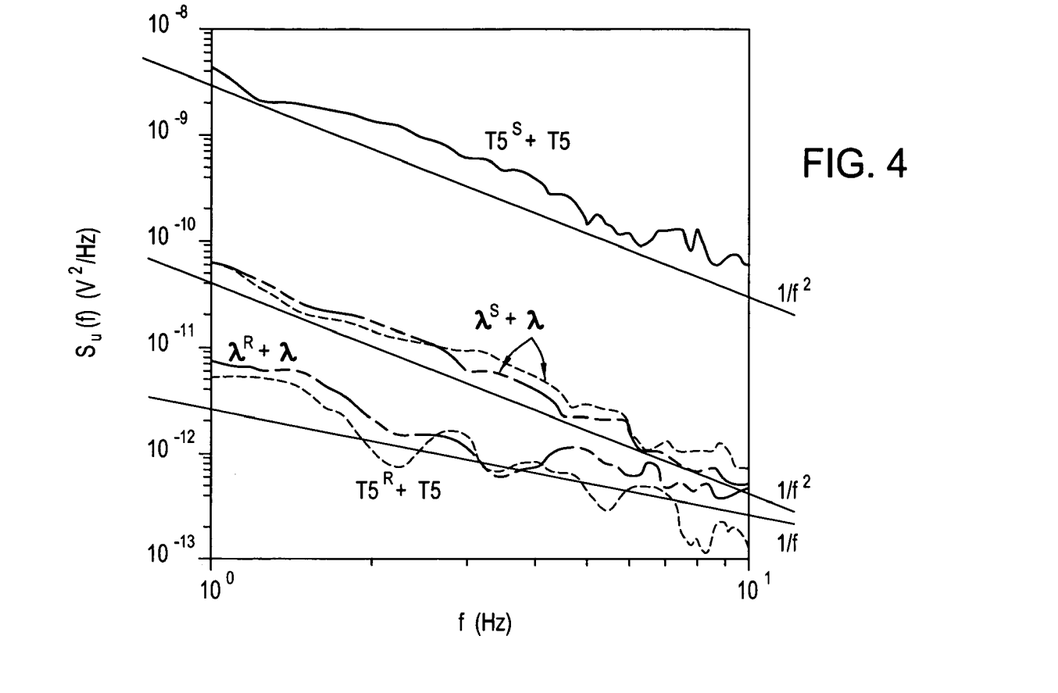
FIG. 4 is a graph with results with bacteriophage lambda.

FIG. 4 is a graph with the results of bacteriophage λ that lack tail fibers and bacteriophage T5. Incubation times were five minutes. In the case of negative response ($\lambda^R$ and $T5^R$), the spectrum of voltage fluctuations in the nano-well roughly follows 1/f shape. In the case of positive response ($\lambda 5^S$ and $T5^S$), the fluctuations are enhanced resulting in a steeper spectrum with a $1/f^2$ like shape.

Figure 5:
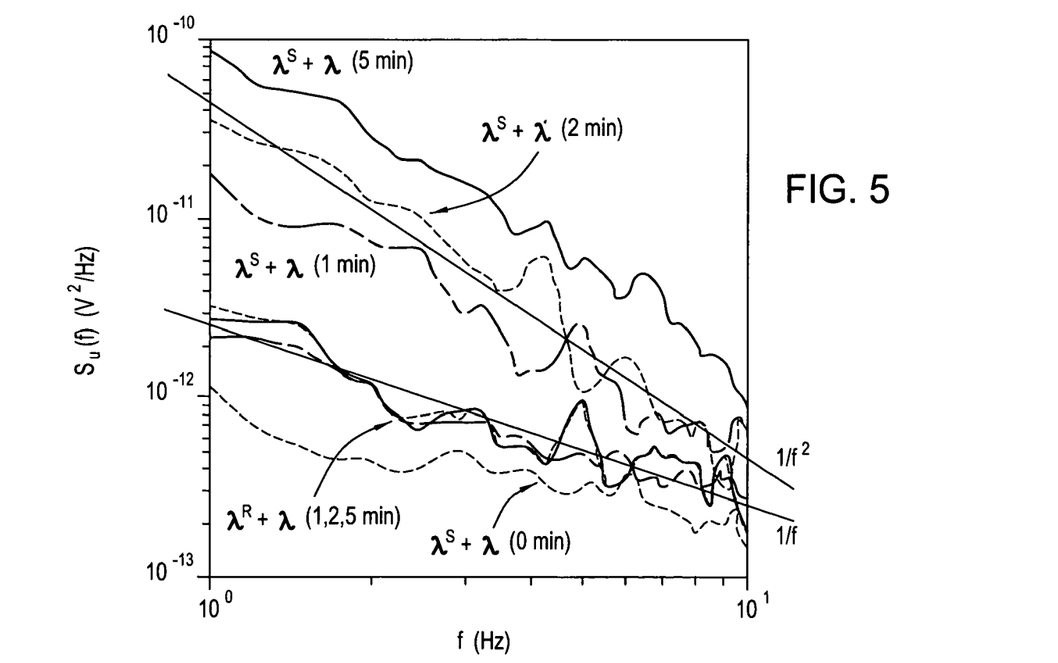
FIG. 5 is a graph with results using a UR-lambda phage.

After the bacteriophage invasion, large and slow stochastic waves were detected with various time and amplitude scales. These fluctuations had power spectra of approximately $1/f^2$ shape in the frequency range of about 1–10 Hz. The real functionality of the detection is expected with bacteriophages possessing tail-fibers. Studies with Ur-λ resulted in high electric fluctuations between about one minute and five minutes pre-incubation times, indicating a fast adsorption process, for only a limited time period (FIG. 5). The presence of tail fibers must accelerate the efficient attachment to the receptors.

FIG. 5 is a graph with the results with the bacteriophage Ur-λ possessing tail fibers. In the non-injecting case, using *Escherichia coli* W3110 (ΔFhuA, ΔlamB) strain ($\lambda^R$), the spectrum is again 1/f like. When the injection event occurs, for incubation times about one minute and greater, a strong $1/f^2$ spectrum appears.

Figure 6:
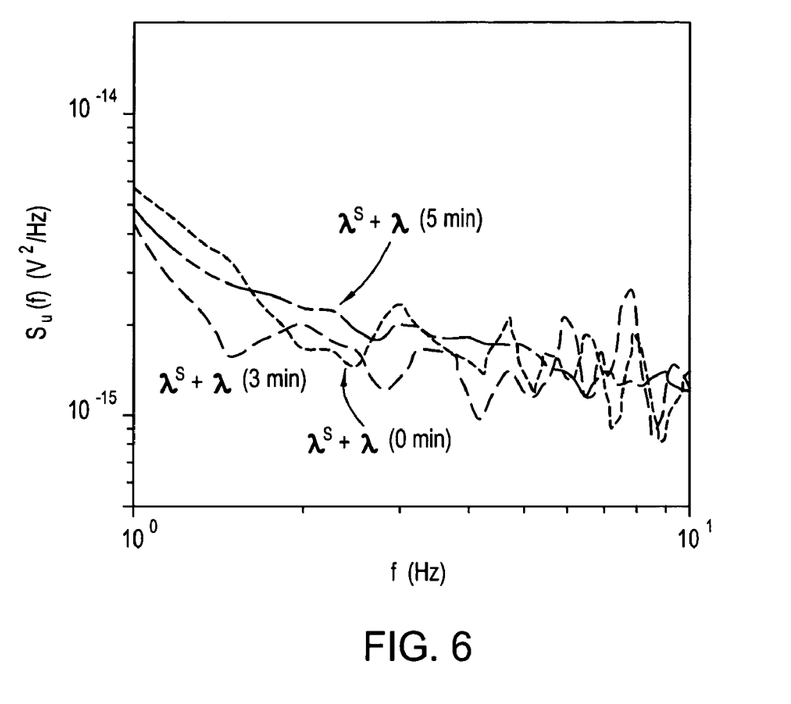
FIG. 6 is a graph of a micro-well spectrum.

Additionally, the spectra of all positive and negative cases were identical in the nano-well device and the micro-well device, see FIG. 6. This result indicates that the fluctuations are random in space and time. As they average out in large detectors, the nano-well or smaller detector systems are required to observe them.

FIG. 6 is a graph that shows the spectrum measured in the micro-well device did not show any observable dependence on bacteriophage infection. This fact indicates that the electrical field fluctuations and the charge density fluctuations are random in space and time, averaging out with the larger detector.

Figure 7A:
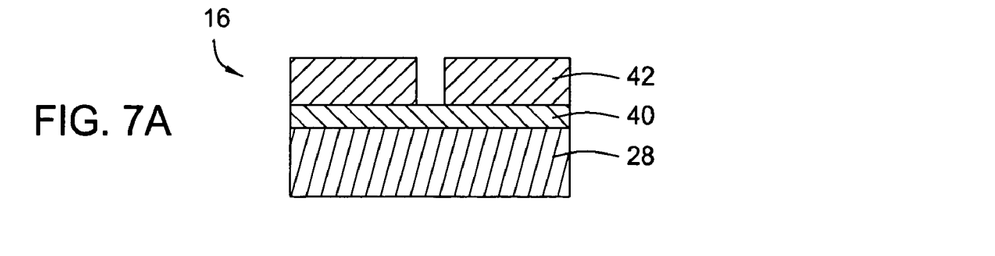
FIGS. 7A–7E shows the steps in the formation of a nanowell.
Figure 7B:
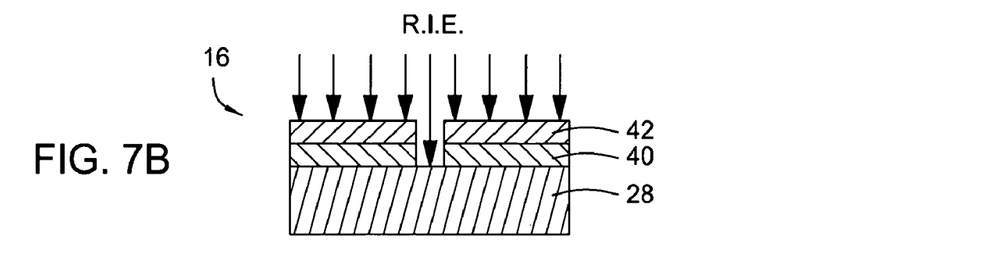
Figure 7C:
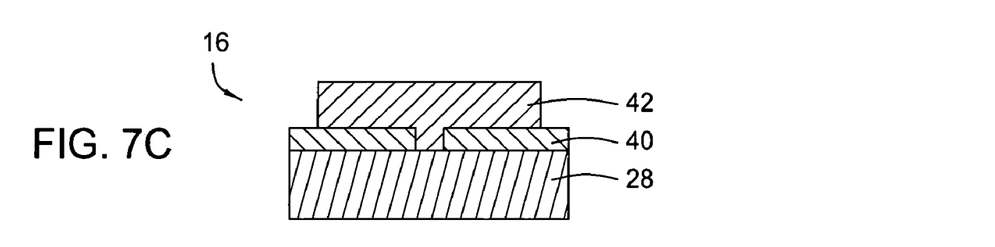
Figure 7D:
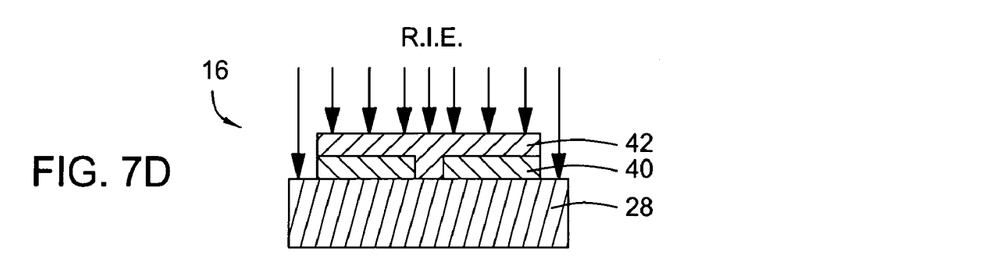
Figure 7E:
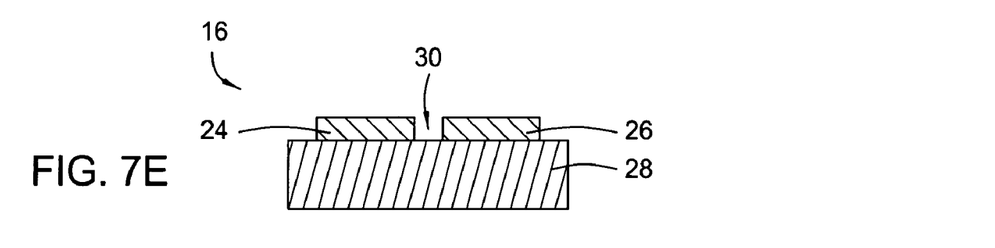

FIGS. 7A–7E shows the steps in the manufacture of the biochip of the present invention. Briefly, a series of lithographic and etching steps are followed as shown to form a nano-well device 16. FIG. 7A illustrates a side view of a contact layer 40 deposited on a substrate layer 28. A sacrificial lithographic layer 42 is printed on the contact layer 40. A directional etch process is used to make an opening through the contact layer 40 through to the substrate layer 28 as illustrated in FIG. 7B. FIG. 7C illustrates a side view of the application of a resist layer 44 to the contact layer 40. A directional etch process is used to remove a portion of the contact layer 40 to the substrate layer 28 as illustrated in FIG. 7D. Once the resist layer 44 is removed the first contact pad 24 and the second contact pad 26 remain on the substrate layer 28 separated by an electrode gap 30 as illustrated in FIG. 7E. In one example, the substrate layer 28 is silicon and the contact layer 40 is titanium. The sacrificial lithographic layer is polymethyl methacrylate printed on the contact layer 40 and a directional etch used to make an opening through the contact layer 40 through to the substrate layer 28. In one example, a 100 nm layer of Titanium is deposited and electron beam lithography and reactive ion etching is used to pattern a 150 nm wide 60 μm long trench. In addition, electron beam lithography and reactive ion etching is used to pattern a 4μ wide 100 μm long bridge. The intersection of the trench and bridge form a 150 nm by 4 μm nano-well.

Figure 8:
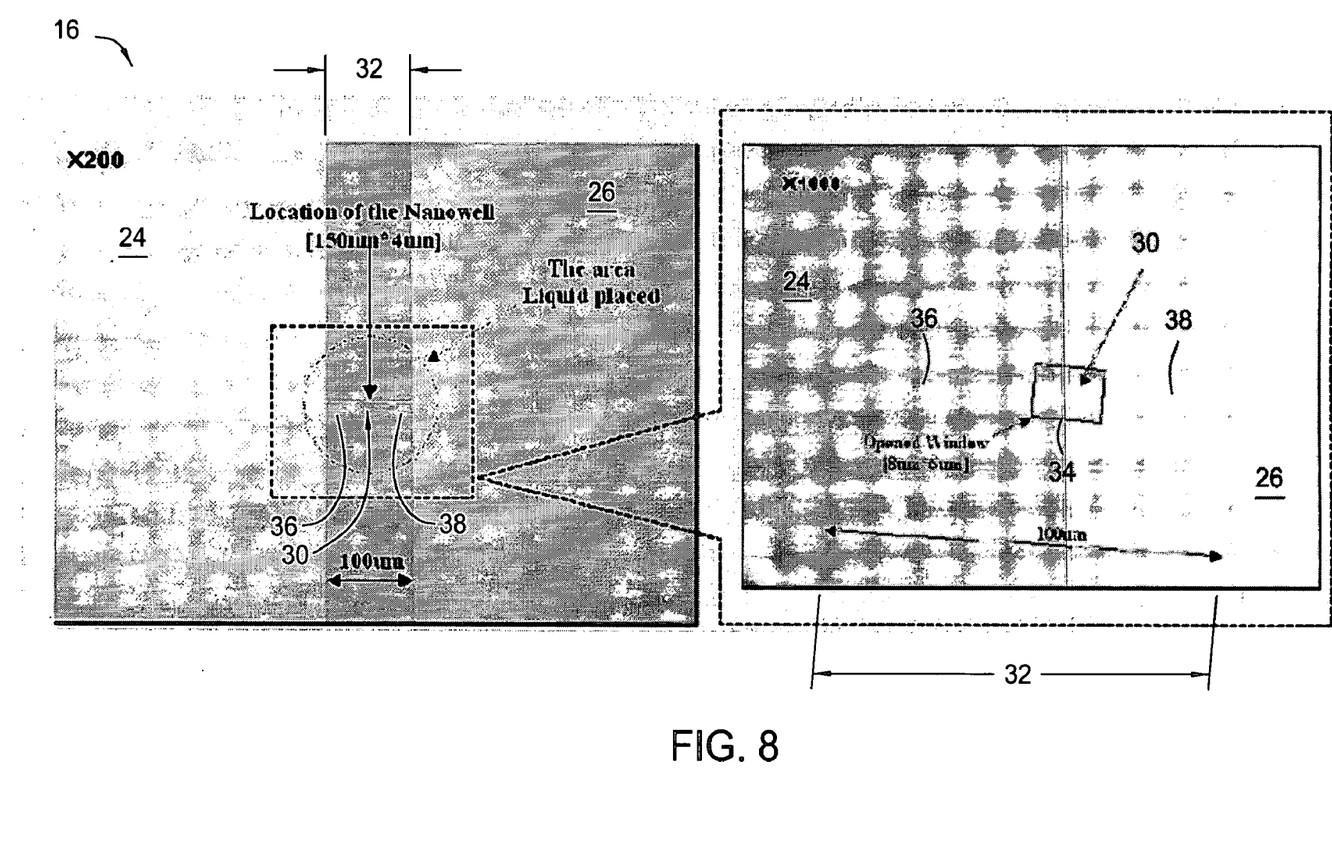
FIG. 8 is a microscope image of the nanoscale detector.

FIG. 8 is a top view of an optical image of the nano-well sensor device 16 of the present invention. A photoresist coating 22 at least partially covers a first contact pad 24 and a second contact pad 26. The first contact pad 24 and the second contact pad 26 are on a substrate layer (not shown). The first contact pad 24 and second contact pad 26 are positioned on the substrate layer (not shown) to form an electrode gap 30. The photoresist coating 22 has a photoresist gap 32 that separates the first contact pad tip 36 and the second contact pad tip 38 which in turn separate the first probe 18 and the second probe 20. The first probe 18 and the second probe 20 are connected to an electrical circuit in the form of a preamplifier module 12 or other circuit (not shown). The nano-well is actually a 150 nm wide and 4 μm long gap in the middle of the bridge, as indicated by FIG. 8.

Figure 9:
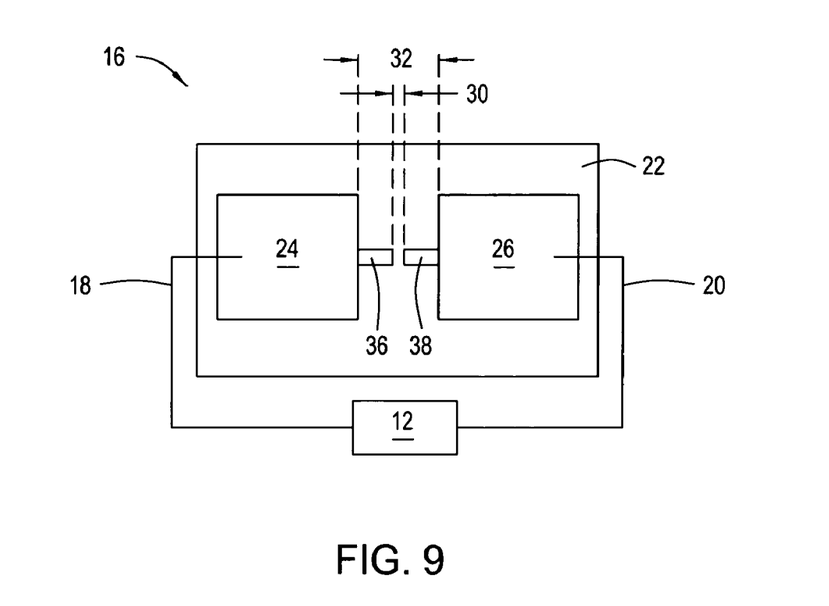
FIG. 9 illustrates a circuit using the present nanoscale detector.

FIG. 9 illustrates a circuit using the present nanoscale detector. FIG. 9 is a top view of the nano-well sensor device 16 of the present invention. A photoresist coating 22 at least partially covers a first contact pad 24 and a second contact pad 26. The first contact pad 24 and the second contact pad 26 are on a substrate layer (not shown). The first contact pad 24 and second contact pad 26 are positioned on the substrate layer (not shown) to form an electrode gap 30. The photoresist coating 22 has a photoresist gap 32 that separates the first contact pad tip 36 and the second contact pad tip 38 which in turn separate the first probe 18 and the second probe 20. The first probe 18 and the second probe 20 are connected to an electrical circuit in the form of a preamplifier module 12 or other circuit. The nano-well is actually a 150 nm wide and 4 μm long gap in the middle of the bridge, as indicated by FIG. 9.

In certain steps etching is preformed and may be accomplished through any compatible technique known to the skilled artisan, e.g., $Cf_4/O_2$ plasma. For example, a Plasma-Therm 790 System may be used at etching conditions of about 150 mbar, 16 standard cubic centimeters per minute (sccm) of $CF_4$ and 0.12 watts per centimeter squared for a total of about five to ten minutes although other suitable parameters may also be used.

The sacrificial lithographic layer may include any compatible substance that may be used as a sacrificial lithographic layer. In one example, the substrate layer 28 is a silicon substrate; however, the substrate layer 28 may also be glass, plastic, polymer, quartz, silicon, sapphire, quartz, silica, silicon carbide, zinc oxide, magnesium oxide, manganese oxide, germanium, gallium nitride, gallium arsenide, gallium phosphide or a metal or combinations thereof. In addition, the substrate may include one or more agents that are bioactive, electrically conductive, thermally conductive, porous, or combinations thereof.

The contact layer 40 may be first contact pad 24 and/or the second contact pad 26 are titanium; however, the contact pads may individually be a metal, a nonmetal, a polymer, a composite, a resist, a resin, a carbon nano-tube, a plastic or combinations thereof. Additionally, the one or more layers may be bioactive, biodegradable, electrically conductive, thermally conductive, porous, stimulatable, or combinations thereof. In addition, more than one layer may be deposited. For example, a second layer of material may be deposited onto the contact layer and the materials may be of dissimilar materials. Alternatively, the contact layer may be of dissimilar materials to produce a first contact pad and a second contact pad of different material. The contact layer may be deposited through a variety of methods including, e.g., electroplating, vapor deposition, spin coating, coating, sputtering, in-situ polymerization or combinations thereof.

In one embodiment of the present invention titanium may be used as a material for the contact layer and in turn the first contact pad and the second contact pad; however, other metals, alloys, doped materials, conductive polymers or metal containing compounds may be used, e.g., gold, silver, platinum, copper, aluminum, tungsten, tantalum, molybdenum, chromium, nickel or the like, alloy thereof or combinations thereof. The metal compound may be titanium nitride, titanium tungsten, tantalum nitride, tungsten nitride, molybdenum nitride or the like.

In addition, the present invention includes the photoresist coating 22 which in one example is AZ5214 under the brand name of Hekisuto K.K.; however, the skilled artisan will recognize that the photoresist coating may be photoimagable polyimides, photoimagable benzocyclobutenes, photoimagable epoxies, novolac based positive photoresists, cardo type photopolymers, A4110, AZ1370 and the like.

Generally, the Debye length (electrostatic screening length) in electrolytes is well below micron. Any static electrical field gets screened with an exponentially decaying tail beyond the Debye length indicating that the physical conditions in electrolytes are not favorable if the ionized object is not in the direct vicinity of the detecting electrodes. For example, a square shaped thin film electrode of about 10 micron size having a concentration of bacteria of about $10^6$ bacteria/mm$^3$ then on the average there is 1 bacterium in a 10 micron size cube. Therefore, only one bacterium is in the vicinity of the electrode and that is not in the direct vicinity because its mean distance from the electrode is several microns. Therefore, a very low ionic signal, e.g., order of magnitudes less than at direct touch, is expected because the electrical field decays exponentially fast beyond the Debye length.

However, if a dc current is forced through the electrolyte between the two electrodes then the situation radically changes and the Debye theory is not applicable and a steady long-range electrical field will expand through the electrolyte. This electrical field will be able to draw the charged (e.g., infected) bacteria to the electrodes where they can be in direct contact with the surface. The great advantage of the method that it attracts only those bacteria which are active (e.g., emitting ions) regarding the SEPTIC detection method. As soon as a given bacterium finished its ion emission and its excess charge gets neutralized, its interaction with the electrical field stops and it will diffuse away from the electrode.

Physical Analysis and the Viability of the Method. Though the details of the dynamics and charge distribution of the ion emission of bacteria is not fully known, simple physical considerations allow some crude estimations about the effectiveness of the enhancement of the sensitivity of the SEPTIC technique. The diffusion coefficient, diffusion time and equilibrium ionization number was already mentioned and the rest of the considerations are new.

The diffusion coefficient of a sphere with radius r in a fluid with viscosity $\eta$ is given by the Stoke's law.

$$D_s = \frac{kT}{6\pi\eta r} \quad (1)$$

For a spherical bacterium with diameter of 1 micron, the diffusion coefficient in water is $$D_B \approx 4.4 * 10^{-13} \left[\frac{m^2}{s}\right] \quad (2)$$

Thus, taking the above example, the diffusion time through the 10 micro size cube (see above) is (see also [3]):

$$\tau_B = \frac{L^2}{D_B} = 227 \, [s]. \quad (3)$$

Because in this practical example, on the average there is only one bacterium in a 10 micron size cube, this result means that, without dc current, during the typical duration (e.g., about 120 seconds) of a SEPTIC measurement, we can measure ions only from a single bacterium. At lower concentrations, we may not even be able to get any bacterium signal.

Charged bacteria emit about $10^8$ ions after the phage infection; however, the net charge is strongly limited by the Coulomb energy. For example, the bacterium is charged up by $Z_B q$ where q is the elementary charge and $Z_B$ is the ionization number, then the total energy needed to it can be estimated as:

$$E_{Cb} \approx \frac{1}{4\pi\varepsilon\varepsilon_0} \frac{Z_B^2 q^2}{r}. \quad (4)$$

The energy needed to add more charge and increase the ionization number by $\Delta Z_B$ can be approximated as follows:

$$E_{\Delta Z} = \frac{dE_{Cb}}{dZ_B}\Delta Z_B = \frac{1}{4\pi\varepsilon\varepsilon_0}\frac{2Z_B q^2}{r}\Delta Z_B. \quad (5)$$

Thus, in the above example of a micron size bacterium, to increase the ionization number by one, results in the following energy:

$$E_1 = \frac{1}{4\pi\varepsilon\varepsilon_0}\frac{2Z_B q^2}{r} \approx 10^{-23} Z_B [J]. \quad (6)$$

First, given a thermally activated ionization process, which is the lowest limit relevant to the actual situation:

$$E_1 \approx kT \approx 4*10^{-21} \, [J], \quad (7)$$

thus [13]:

$$Z_{max,eq} \approx \frac{kT 4\pi\varepsilon\varepsilon_0 r}{2q^2} \approx 812. \quad (8)$$

However, which was not considered in [13] is the fact that driven nonequilibrium systems do not have this limitation so the actual ionization number may be much larger. Given, the ion emission is driven by an electrochemical force with a characteristic energy of 1 eV:

$$E_1 = 1.6*10^{-19} \, [j] \quad (9)$$

and $$Z_{max,eq} \approx \frac{E_1 4\pi\varepsilon\varepsilon_0 r}{2q^2} \approx 31400 \quad (10)$$

the maximum ionization number of bacteria with 1 micron size is in the range of 1000–30,000.

Estimation of the electrical transport properties versus the ionization number. The application of the Einstein equation between the mobility and the diffusion constant yields:

$$\mu_B = \frac{Z_B q D_B}{kT}. \quad (11)$$

The drift velocity of charged bacteria in a dc electrical field $E_{dc}$ is:

$$u_d = \mu_B * E_{dc} = \frac{Z_B q D_B}{kT} E_{dc}. \quad (12)$$

At 1 V/m electrical field with a 1 micron size bacteria charged to 10,000 q results in:

$$u_d \approx 1.8*10^{-7} \left[\frac{m}{s}\right]. \quad (13)$$

At 1000 V/m electrical field, e.g., the length scale of 100 microns by a voltage of 0.1 V, the drift velocity is 0.18 mm/second, so all bacteria in the 100 micron length range would be collected at the electrodes within less than a second. Therefore, the bacteria can be drifted through the fluid and collected at the electrode with a high speed.

The current density of bacterium number is:

$$J_{Bnumber} = n_B u_d = n_B \mu_B E_{dc} = \frac{Z_B q D_B n_B}{kT} E_{dc}. \quad (14)$$

If the dc current I is dominated by the background ion current in the fluid, then:

$$E_{dc} \propto I_{cc}. \quad (15)$$

That is the bacterium current density will satisfy:

$$J_B \propto I_{dc}. \quad (16)$$

The estimation of the signal enhancement is not easy without exactly knowing the mechanism of the generation of the ion cascades and the possible influence of electrical field on that. However, a simple estimation can be made by using the fact that the observed fluctuations have $1/f^2$ type power density spectrum. Then the acceleration of the bacterium flow with increased currents can contribute to an accelerated fluctuation. A recorded $1/f^2$ noise with spectrum $A/f^2$ has a spectrum of $k^2 A/f^2$ when it is played back with a speed increased by a factor of K because of the f=>Kf transformation. Thus, from the above argumentation, the spectrum will scale as:

$$S_{u,accelerated}(f) \propto J_B^2 \propto I_{dc}^2. \quad (17)$$

There is more than just playing the fluctuations faster at increased currents. The electrodes will accumulate a larger number of bacteria within the lifetime of ion cascades which implies also an increased amplitude of the fluctuations due to cross-correlation effects. If this increase scales linearly with the bacterium current density JB that effect will also result in a scaling of the power density spectrum by $I^2$. Then, due to the two separate effects:

$$S_u(f) \propto J_B^4 \propto I_{dc}^4. \quad (18)$$

In addition, the two effects outlined above may be two sides of a single physical mechanism, (e.g., not independent or in other cases the space charge of the bacteria the second effect may saturate at a certain current density, frequency and after a characteristic time of saturation) thus it is proper to conclude the estimation as:

$$S_u(f) \propto I_{dc}^X. \quad (19)$$

where $2 \leq X \leq 4$.

It is important to note that the scaling/enhancement of the power spectrum described by Equation. 19 is relevant for the already increased signal due to the removal of the Debye screening because the "active" bacteria are touching the electrode when there is a dc current. For Example, a Debye screening length of 0.25 micron and, in the case of zero dc current, an effective distance of 3 microns of the bacterium from the electrode, then the dc current situation with the bacterium touching the electrode provides about exp[3/0.25] ≈15,000 times enhanced electrical field. The amplification based on removing Debye screening works with full strength only up to the first layers of bacteria over the electrode because the next layers will suffer increasing Debye screening.

Finally, this simple picture suggests that, in the case of a fixed current and electrode sizes, an increasing gap size between the electrodes will result in an increasing efficiency of this enhancement technique.

The technique of feeding the electrodes by a dc current generator, and so letting a dc current through the electrolyte, can increase the sensitivity of SEPTIC by several orders of magnitude. The results indicate that the gap size does not have to be in the nanometer range and a larger gap size can make enhancement more efficient.

Finally, it is important to note that the present approach/calculations are strongly simplified and taking into the account Debye's electrophoresis theory can significantly refine them.

The substrate used in the present invention may be a generally transparent substance including glass, plastic, polymer, or combinations thereof. Generally used materials may include one or more of the following: Si, single-crystal Si, a silicon nitride composition (SiNx), a silicon oxide composition (SiOx), or titanium (Ti) deposited between the substrate and the first layer, between layers or combinations thereof.

In accordance with the present invention, a wide variety of photoimagable polymers may be used such as photoimagable polyimides, photoimagable benzocyclobutenes, photoimagable epoxies, novolac based positive photoresists, cardo type photopolymers, and the like. Difunctional epoxy compounds may also be used including diglycidyl ethers of Bisphenol A (e.g., those available under the trade designations "Epon 828", "Epon 1004", "Epon 1001F", "Epon SU-8" and "Epon 1010" from Shell Chemical Co., "DER-331", "DER-332", and "DER-334" from Dow Chemical Co.), 3,4-epoxycyclohexylmethyl-3,4-epoxycyclohexene carboxylate (e.g., "ERL-4221" from Union Carbide Corp.), 3,4-epoxy-6-methylcyclohexylmethyl-3,4-epoxy-6-methylcyclohexene carboxylate (e.g., "ERL-4201" from Union Carbide Corp.), bis(3,4-epoxy-6-methylcyclohexylmethyl) adipate (e.g., "ERL-4289" from Union Carbide Corp.), bis(2,3-epoxycyclopentyl) ether (e.g., "ERL-0400" from Union Carbide Corp). Additionally, the increase of the fluctuations is not thermal noise or thermal equilibrium process. The fluctuation is generated by an excess source of energy and not by thermal equilibrium energy fluctuations. Typically the current is about 10–13 A that is about 106 electrons/second into the nanowell electrodes. Given the conductivity of the nano-well with the fluid is about 100 times greater, that corresponds to about 108 effective ions/second transport in the fluid. For example:

Amplifier input (with cables):

$$R \approx 10^8 \Omega \quad C = 10^{-9} \text{ F} \quad (20)$$

$$S_{u,th} = 4kT\text{Re}Z(f) \cong 4kTR_{eff}(f) \cong 4.8*10^{-18}*R_{eff}(f) \quad (21)$$

For $10^8$ Ohm, that would give 5 times greater Su at 1 Hz than what we measure at the strongest phage reaction and 100 times greater than what we measure in the negative experiments. Because the negative experiments can be considered as equilibrium systems, the results indicate that the Reff is around 1 MOhm at 1 Hz, in the nano-well. Conductivity with m different kinds of ions in the fluid:

$$\sigma = e z_1 n_1 \mu_1 + e z_2 n_2 \mu_2 + \ldots e z_m n_m \mu_m \quad (22)$$

Given $R_{eff} \alpha 1/\sigma$ and that the concentration of the original ions in the water does not decrease due to the phage infection, then the conductivity can only increase, consequently the resistance and the thermal noise can only decrease.

Using any of the devices shown herein and variations there, the present invention may be used with a system and method to detect and identify any bacteria provided the availability of the corresponding bacteriophage(s). The method is very fast with infection occuring within a minute. The whole electronics can be integrated on a biochip so the device can be as small as a pen. Therefore, the device can be a versatile portable instrument. In addition, the skilled artisan will recognize that many other architectures may be used, e.g., a JFET, a MOSFET, an OSFET or an SPR sensor.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

1. Ackermann, H.-W. and M. S. DuBow. 1987. General properties of bacteriophages, p. 143–172. In Viruses of prokaryotes. CRC Press, Boca Raton Fla.
2. Ahmed, R., C. Bopp, A. Borczyk, and S. Kasatiya. 1987. Phage-typing scheme for *Escherichia coli* O157:H7. J. Infect. Dis. 155:806–809.
3. Ahmed, R., P. Sankar-Mistry, S. Jackson, H. W. Ackermann, and S. S. Kasatiya. 1995. *Bacillus cereus* phage typing as an epidemiological tool in outbreaks of food poisoning. J. Clin. Microbiol. 33:636–640.
4. Boulanger, P. and L. Letellier. 1988. Characterization of ion channels involved in the penetration of phage T4 DNA into *Escherichia coli* cells. J. Biol. Chem. 263:9767–9775.
5. Daugelavichius, R. I., V. T. Iagminas, L. L. Grinius, and R. S. Ptashekas. 1987. [Formation of ion channels in the *Escherichia coli* cytoplasmic membrane after exposure to bacteriophages T4 and lambda]. Biokhimiia. 52:1059–1067.
6. Gilbert, R. J. and J. M. Parry. 1977. Serotypes of *Bacillus cereus* from outbreaks of food poisoning and from routine foods. J. Hyg. (Lond) 78:69–74.
7. Goldberg E. B., Grinius L., and L. Letellier. 1994. Recognition, Attachment and Injection, p. 347–357. In J. D. Karam, J. W. Drake, K. N. Kreuzer, G. Mosig, D. H. Hall, F. A. Eiserling, L. W. Black, E. K. Spicer, E. Kutter, K. Carlson, and E. S. Miller (eds.), Molecular biology of bacteriophage T4. American Society for Microbiology, Washington D.C.
8. Kasatiya, S. S. and P. Nicolle. 1978. Phage typing, p. 669–715. In A. I. Laskin and H. A. Lechevalier (eds.), CRC handbook of microbiology. CRC Press, West Palm Beach Fla.
9. Labedan, B., K. B. Heller, A. A. Jasaitis, T. H. Wilson, and E. B. Goldberg. 1980. A membrane potential threshold for phage T4 DNA injection. Biochem. Biophys. Res. Commun. 93:625–630.
10. Tadigadapa, S. Integration of micromachined devices and microelectronic circuits: techniques and challenges. Proc. 43rd Midwest Symp. on Circuits and Systems, Lansing, Mich., Aug. 8–11, 2000.224–227. 2000. Ref Type: Serial (Book, Monograph)
11. Taylor, A. J. and R. J. Gilbert. 1975. *Bacillus cereus* food poisoning: a provisional serotyping scheme. J. Med. Microbiol. 8:543–550.
12. Vaisanen, O. M., N. J. Mwaisumo, and M. S. Salkinoja-Salonen. 1991. Differentiation of dairy strains of the *Bacillus cereus* group by phage typing, minimum growth temperature, and fatty acid analysis. J. Appl. Bacteriol. 70:315–324.
13. L. B. Kish, S. M. Bezrukov, A. Der, M. Cheng, M. D. King, R. Young, S. Seo and J. U. Kim. Physics behind the new technique "Sensing of phage-triggered ion cascades" (SEPTIC) for the prompt identification of bacteria, Proc. SPIE's Third International Symposium on Fluctuations and Noise, Conference on Noise and Information in Nanoelectronics, Sensors and Standards III, (2005), in press.

What is claimed is:

1. An apparatus comprising:
   a nano-well device comprising one or more input/output connections about a gap; and
   one or more bacteriophages at or about the gap that trigger a detectable electrical field fluctuation when the one or more bacteriophages contact a cognate target within a liquid sample.

2. The apparatus of claim 1, wherein the gap is between about 50 to about 500 nanometers.

3. The apparatus of claim 1, wherein the one or more input/output connections comprises a FET, a JFET, a MOSFET, an OSFET or an SPR sensor.

4. The apparatus of claim 1, wherein the one or more input/output connections are in electrical communication with an amplifier, a preamplifier, a contact, a switch, a transistor and combinations thereof.

5. The apparatus of claim 1, wherein the one or more input/output connections comprise ball bonds, wire bonds, tape bonds, chisel bonds and combinations thereof.

6. The apparatus of claim 1, wherein the detectable electrical field fluctuation comprises a power density spectra of about $1/f$, $1/f^2$ shape and combinations thereof.

7. The apparatus of claim 1, wherein contact between the one or more bacteriophages and the cognate target causes stochastic waves with various time and amplitude scales.

8. The apparatus of claim 1, wherein contact between the one or more bacteriophages and the cognate target causes one or more stochastic fluctuations comprising a power spectra with approximately an $1/f^2$ shape in the frequency range of about 1 Hz and about 10 Hz.

9. The apparatus of claim 1, wherein the cognate target for the phage comprises one or more bacteria selected from *Escherichia, Enterobacter, Salmonella, Staphylococcus, Shigella, Listeria, Aerobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus, Bordetella* and combinations thereof.

10. The apparatus of claim 1, wherein the one or more bacteriophages comprise *S. mutans* phages, *Bacillus* phage Φ29, *Actinomyces* phages, bacteriophage M102, bacteriophage e10, bacteriophage f1, bacteriophage λ, bacteriophage PI, spherical phage PhiX174, spherical phage G4, spherical phage S13, bacteriophage T1, bacteriophage T2, bacteriophage T3, bacteriophage T4, bacteriophage T5, bacteriophage T6, bacteriophage T7, ssRNA bacteriophages MS2, ssRNA bacteriophages R17, ssRNA bacteriophages f2, ssRNA bacteriophages Q beta and combinations thereof.

11. A method for detecting bacteria comprising the steps of:
contacting a nano-well device comprising one or more input/output connections about a gap with one or more bacteriophages at or about the gap with a liquid sample; and
detecting one or more electrical field fluctuations produced when one or more bacteriophages contact a cognate target within the sample, whereby the one or more electrical field fluctuations in the sample at the gap demonstrate the present of absence of the cognate target within the sample.

12. The method of claim 11, wherein contact between the one or more bacteriophages and the cognate target causes one or more stochastic fluctuations comprising a power spectra with approximately an $1/f^2$ shape in the frequency range of about 1 Hz and about 10 Hz.

13. The method of claim 11, wherein the cognate target comprises one or more bacteria selected from *Escherichia, Enterobacter, Salmonella, Staphylococcus, Shigella, Listeria, Aerobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus, Bordetella* and combinations thereof.

14. The method of claim 11, wherein the one or more bacteriophages comprise *S. mutans* phages, *Bacillus* phage Φ29, *Actinomyces* phages, bacteriophage M102, bacteriophage e10, bacteriophage f1, bacteriophage λ, bacteriophage PI, spherical phage PhiX174, spherical phage G4, spherical phage S13, bacteriophage T1, bacteriophage T2, bacteriophage T3, bacteriophage T4, bacteriophage T5, bacteriophage T6, bacteriophage T7, ssRNA bacteriophages MS2, ssRNA bacteriophages R17, ssRNA bacteriophages f2, ssRNA bacteriophages Q beta and combinations thereof.

15. A nano-well sensor comprising:
a substrate; a nanowell device disposed on the substrate, wherein the nanowell device comprises one or more input/output connections about a gap and one or more bacteriophages at or about the gap that trigger a detectable electrical field fluctuation when the one or more bacteriophages contact a cognate target within a liquid sample.

16. A method for making a nano-well sensor comprising the steps of:
forming on a substrate one or more input/output connections about a gap; and
providing one or more bacteriophages at or about the gap that trigger a detectable electrical field fluctuation when the one or more bacteriophages contact a cognate target within a liquid sample.

17. The method of claim 16, wherein the substrate comprises glass, plastic, polymer, quartz, silicon, sapphire, quartz, silica, silicon carbide, zinc oxide, magnesium oxide, manganese oxide, germanium, gallium nitride, gallium arsenide, gallium phosphide or a metal or combinations thereof.

18. The method of claim 16, wherein the step of forming on a substrate one or more input/output connections comprises electroplating, vapor deposition, spin coating, coating, sputtering, in-situ polymerization or combinations thereof.

19. The method of claim 16, wherein the one or more input/output connections comprise a metal, a nonmetal, a polymer, a composite, a resist, a resin, a carbon nano-tube, a plastic or combinations thereof.

20. The method of claim 16, wherein the gap is positioned for exposure to the liquid sample.

21. The method of claim 16, further comprising an insulating layer deposited on at least a portion of the one or more input/output connections.

22. The method of claim 16, wherein the cognate target comprises one or more bacteria selected from *Escherichia, Enterobacter, Salmonella, Staphylococcus, Shigella, Listeria, Aerobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus, Bordetella* and combinations thereof.

23. The method of claim 16, wherein the one or more bacteriophages comprise *S. mutans* phages, *Bacillus* phage Φ29, *Actinomyces* phages, bacteriophage M102, bacteriophage e10, bacteriophage f1, bacteriophage λ, bacteriophage PI, spherical phage PhiX174, spherical phage G4, spherical phage S13, bacteriophage T1, bacteriophage T2, bacteriophage T3, bacteriophage T4, bacteriophage T5, bacteriophage T6, bacteriophage T7, ssRNA bacteriophages MS2, ssRNA bacteriophages R17, ssRNA bacteriophages f2, ssRNA bacteriophages Q beta and combinations thereof.

* * * * *